United States Patent

Hamprecht et al.

Patent Number: 5,750,761
Date of Patent: May 12, 1998

[54] CYANATION OF DOUBLE BOND SYSTEMS

[75] Inventors: Rainer Hamprecht, Odenthal; Claudia Müller, Köln, both of Germany

[73] Assignee: Bayer Aktiengesellschaft, Leverkusen, Germany

[21] Appl. No.: 608,455

[22] Filed: Feb. 28, 1996

[30] Foreign Application Priority Data

Mar. 3, 1995 [DE] Germany .......................... 19 507 415.7
Mar. 14, 1995 [DE] Germany .......................... 19 509 043.8

[51] Int. Cl.$^6$ .......................................... C07C 255/03
[52] U.S. Cl. .................................................. 558/423
[58] Field of Search ..................................... 558/423

[56] References Cited

U.S. PATENT DOCUMENTS 4,578,469  3/1986  Deger et al. ........................ 546/66

FOREIGN PATENT DOCUMENTS 0 027 529 A1  4/1981  European Pat. Off. .
0 065 743 A1  12/1982  European Pat. Off. .
2006253  5/1979  United Kingdom .

OTHER PUBLICATIONS

P. Sykes, "A guidebook to Mechanism in Organic Chemistry" pp. 348–351, 5th ed. Long Man, New York. (1981).
P. Sykes, "Reaktionsmechanismem der Organischen Chemie", 9th Ed. pp. 426–429 VCH, Verlagsgesellschaft (1988).
Dewert 27360 D/16=J5 (6059–872)–Sep. 16, 1980.

*Primary Examiner*—Johann Richter
*Assistant Examiner*—Ebenezer Sackey
*Attorney, Agent, or Firm*—Sprung Kramer Schaefer & Briscoe

[57] ABSTRACT

A process for the preparation of compounds of the formula

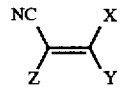

wherein the substituents X, Y and Z have the meaning given in the description, by reaction of compounds of the formula

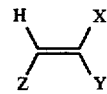

with a cyanide and an oxidizing agent other than $Br_2$ in the presence of halides which offers industrial hygiene advantages and renders possible large-scale industrial access to dyestuff syntheses has been found.

15 Claims, No Drawings

CYANATION OF DOUBLE BOND SYSTEMS

The present invention relates to a process for the cyanation of double bond systems.

A process for cyanation of double bond systems in which the bromine used in particular as an oxidizing agent has certain disadvantages with regard to its use is already known from DE-A 2 844 299 (GB-A-2 006 253). The object of the present invention was to overcome these disadvantages.

A process has now been found for the preparation of compounds of the formula I

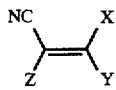

wherein

X and Y independently of one another represent an electron-attracting radical, or X and Y, together with the carbon atom to which they are bonded, form an optionally substituted heterocyclic or carbocyclic ring, where the carbocyclic radical is preferably 5- to 7-membered and optionally is substituted and/or contains one or more carbonyl groups, Z represents optionally substituted, optionally fused aryl or represents an optionally substituted, optionally fused heterocyclic radical, or Y and Z, together with the carbon atoms to which they are bonded and including the double bond, form an optionally substituted heterocyclic radical, characterized in that compounds of the formula

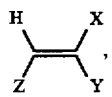

wherein

X, Y and Z have the abovementioned meaning, are reacted with a cyanide or a cyanide-donating compound and then with an oxidizing agent other than $Br_2$ in the presence of halides.

X and Y preferably independently of one another represent a radical of which the Hammett substituent constant σ (para)>0.

An appropriate list of Hammett substituent constants is to be found, for example, in Sykes, Reaktionsmechanismen der organischen Chemie (Reaction mechanisms of organic chemistry), 9th edition Weipheim, VCH Verlagsgesellschaft, 1988, or can be determined by known processes.

A preferred embodiment of the process according to the invention is characterized in that compounds of the formula II are reacted with a cyanide or a cyanide-donating compound and then with an oxidizing agent other than $Br_2$ in the presence of halides and acid.

The process according to the invention is preferably used for the preparation of compounds of the formula I wherein X denotes —CN, —CO—OV$_1$.

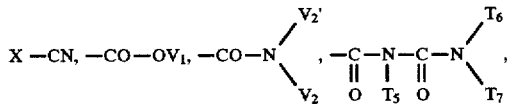

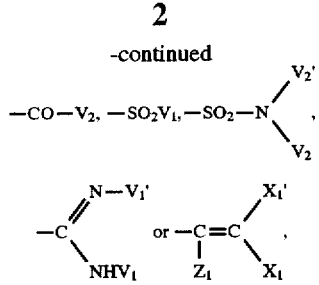

wherein $V_1$ and $V_1'$ independently of one another represent alkyl, cycloalkyl, alkenyl, aralkyl or aryl, $T_5$, $T_6$ and $T_7$ independently of one another denote hydrogen or unsubstituted or substituted aryl, in particular phenyl, $V_2$ and $V_2'$ independently of one another represent H or $V_1$, or $V_1$ and $V_1'$ or $V_2$ and $V_2'$, in each case together with the radicals to which they are bonded, represent a 5- or 6-membered, optionally substituted unsaturated, preferably aromatic heterocyclic radical which contains 1 to 3 identical or different hetero atoms from the series consisting of O, N and S and is optionally fused by a substituted or unsubstituted benzene ring, or represent a 5- or 6-membered, optionally substituted unsaturated carbocyclic radical, preferably phenyl, $X_1$ and $X_1'$ independently of one another represent,

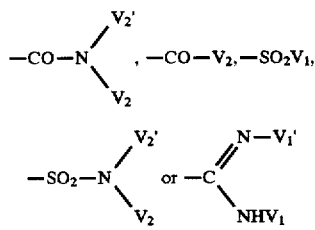

wherein $V_1$, $V_1'$, $V_2$ and $V_2'$ have the abovementioned meaning, or $X_1$ and $X_1'$, together with the C atom to which they are bonded, represent a 5- or 6-membered, optionally substituted heterocyclic radical which contains 1 or 2 N atoms and is optionally fused by a further 5-membered unsaturated heterocyclic radical or a benzene ring, $Z_1$ represents optionally substituted $C_6$–$C_{10}$-aryl, which is optionally fused by a saturated or unsaturated heterocyclic radical, or represents an unsaturated 5- or 6-membered, optionally substituted heterocyclic radical which contains 1 to 4 identical or different hetero atoms from the series consisting of O, N and S and can be fused by a benzene ring, or $Z_1$ and $X_1$, together with the carbon atoms to which they are bonded and including the double bond, form an optionally substituted and optionally fused heterocyclic radical or an aromatic carbocyclic ring, in particular a benzene ring, Y is identical to or different from X, or X and Y, together with the C atom to which they are bonded, represent a 5- or 6-membered optionally substituted heterocyclic radical which contains 1 or 2 N atoms and which can optionally be fused by a further 5-membered unsaturated heterocyclic ring or a benzene ring, Z represents optionally substituted $C_6$-/$C_{10}$-aryl, which can optionally be fused by a saturated or unsaturated heterocyclic radical, or represents an unsaturated 5- or 6-membered optionally substituted heterocyclic radical which contains 1 to 4 identical or different hetero atoms from the series consisting of O, N and S and can be fused by a benzene ring, or Y and Z together, including the double bond to which they are bonded, form a 6-membered, optionally substituted heterocyclic radical which contains a hetero atom from the series consisting of O, N and S and is optionally fused by a substituted or unsubstituted benzene ring, where possible substituents for a carbocyclic and a heterocyclic radical are, in particular, alkyl, alkylsulphonyl, aryl, aralkyl, alkenyl, —SO$_2$OR$_1$, cycloalkyl, alkoxy, alkoxycarbonyl, acyl, halogen, cyano, C=O, C=NH, in each case optionally substituted carboxamide or sulphonamide, nitro or exocyclic =O or =NH, and possible substituents for the fused benzene ring are, in particular, alkyl, SO$_2$-alkyl, optionally substituted sulphonamide-SO$_2$NR$_2$R$_2$, alkyl, aralkyl, cycloalkyl, alkoxy, alkoxycarbonyl, acyl, halogen, cyano, nitro or alkenyl.

Possible substituents for the aromatic carbocyclic radical or the heterocyclic radical in the definition of Z are, in particular,

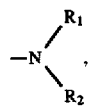

OR$_1$, NHCOR$_1$ and NHSO$_2$R$_1$, in which

R$_1$ and R$_2$ independently of one another represent hydrogen, optionally substituted alkyl, alkenyl, cycloalkyl, aralkyl or aryl, or R$_1$ and R$_2$, together with the nitrogen atom to which they are bonded, form a 5- to 6-membered heterocyclic radical having 1 to 3 hetero atoms from the series consisting of O, N and S.

The process according to the invention is preferably used for the preparation of compounds of the formula

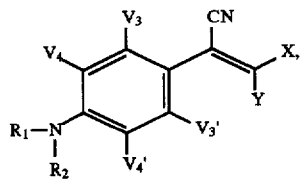

wherein

X, Y, R, and R$_2$ have the abovementioned meaning,

V$_3$ and V$_3$' independently of one another represent H, C$_1$–C$_4$-alkyl, C$_1$–C$_4$-alkoxy, —Cl, Br or —OCO—C$_1$–C$_4$-alkyl, V$_4$ and V$_4$' independently of one another represent H, C$_1$–C$_4$-alkyl or C$_1$–C$_4$-alkoxy, or V$_3$ and V$_4$' including the ring C atoms to which they are bonded, form a 6-membered carbocyclic radical, and/or V$_3$' and V$_4$', including the ring C atoms to which they are bonded, form a 6-membered carbocyclic radical, and/or R$_1$ and/or R$_2$ with V$_4$ and/or V$_4$' together form the remaining members of a tetrahydro pyridine, dihydropyridine or quinolizine ring.

Compounds of the formula (I) which are particularly preferably prepared by the process according to the invention are those in which Y and Z, including the double bond, form a coumarin ring. These compounds correspond to the formula (IV)

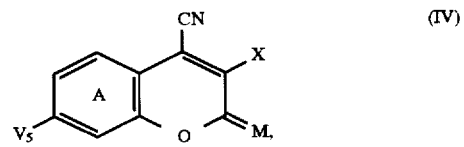

in which

V$_5$ represents

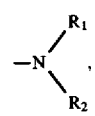

OR$_1$, NHCOR$_1$ or NHSO$_2$R$_1$,

R$_1$ and R$_2$ independently of one another represent hydrogen, optionally substituted alkyl, cycloalkyl, aralkyl or aryl, or R$_1$ and R$_2$, together with the nitrogen atom to which they are bonded and optionally including further hetero atoms, form a 5- to 7-membered heterocyclic radical, or one of the radicals R$_1$ or R$_2$, with a carbon atom of ring A in the opposition relative to the amino group, forms a fused-on, saturated, optionally substituted 5- or 6-membered ring, M represents =NR$_3$, =NCOR$_4$,

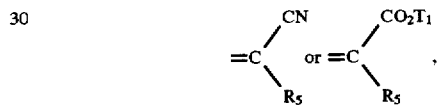

in particular =NH or =O, wherein

R$_3$ represents alkyl or optionally substituted phenyl,

R$_4$ represents optionally substituted alkyl, aralkyl, aryl, vinyl, alkoxy, phenoxy or amino and R$_5$ represents carbalkoxy, cyano or optionally substituted carboxamide, or R$_5$, together with the substituent X, forms the remaining members of an unsaturated 6-membered, optionally fused N-heterocyclic radical, and X has the abovementioned meaning.

Possible electron-attracting radicals X are, above all:

—CN, —COOV$_1$, wherein V$_1$ represents alkyl, in particular C$_1$–C$_6$-alkyl,

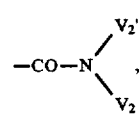

wherein V$_2$ and V$_2$' have the abovementioned meaning,

—SO$_2$V$_1$, wherein V$_1$ represents alkyl or aryl, or one of the following radicals:

a)

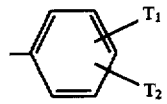

wherein

T$_1$ represents cyano or nitro and $T_2$ represents hydrogen, cyano, halogen, alkylsulphonyl, optionally substituted sulphonamide, in particular substituted by alkyl, or nitro, b)

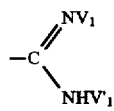

wherein
$V_1$ and $V_1'$ independently of one another denote an optionally substituted $C_1$–$C_{10}$-alkyl, $C_3$–$C_7$-cycloalkyl, $C_6$–$C_{10}$-Ar-$C_1$–$C_{10}$-alkyl- or $C_6$–$C_{10}$-aryl radicals.

c)

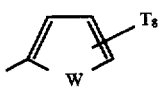

wherein
$T_8$ represents hydrogen, alkoxycarbonyl, optionally substituted carboxamide or cyano and
W represents oxygen or sulphur, d)

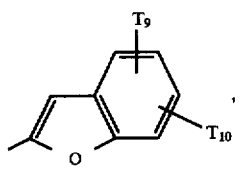

e)

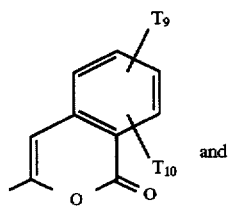

f)

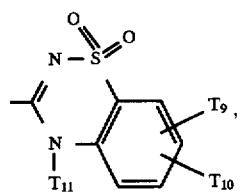

wherein, in the formulae d), e) and f),
$T_9$ represents hydrogen, alkyl, chlorine, bromine or alkoxy,
$T_{10}$ represents hydrogen or alkyl and
$T_{11}$ represents acyl or an optionally substituted $C_1$–$C_4$-alkyl or phenyl radical, but preferably represents hydrogen, g) an optionally substituted, in particular fused pyrazole, imidazoie, thiazole, oxazole, 1,2,4-triazole, 1,3,4-oxadiazole, 1,3,4-thiiadiazole, quinoxalone, quinazolone, benzoimidazole, benzoxazole, benzothiazole, pyridine, quinoline or pyrimidine ring which is bonded to the coumarin ring, in the adjacent position to a ring nitrogen atom, such as, for example,

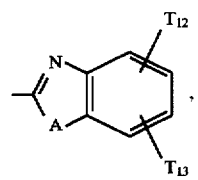

wherein
A represents oxygen, sulphur or the grouping

$T_{14}$ represents hydrogen, alkyl or, aralkyl,
$T_{12}$ represents hydrogen, alkyl, halogen, alkoxy, $NHCOR_1$ or $NHSO_2R_1$,
$T_{13}$ represents hydrogen or alkyl or
$T_{12}$ and $T_{13}$ together can also form a further fused-on optionally substituted aromatic ring; preferred radicals are benzothiazole, benzoxazole or benzimidazole radicals wherein the benzene radical is optionally further substituted by Cl, —$NHSO_2CH_3$ or $CH_3$, and wherein $T_{14}$, together with $R_5$, can form the remaining members of an N-heterocyclic radical, h)

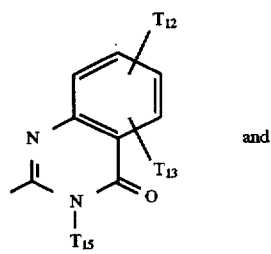

and i)

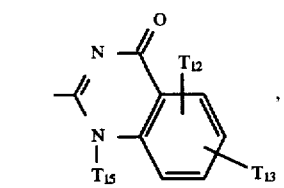

wherein
$T_{12}$ and $T_{13}$ have the abovementioned meaning and
$T_{15}$ is hydrogen or optionally substituted alkyl or phenyl, and j)

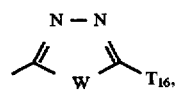

wherein
W is oxygen or sulphur and
$T_{16}$ denotes optionally substituted alkyl, cycloalkyl, aralkyl, phenyl or pyridyl.

The substituents $V_1$, $V_1'$, $T_1$–$T_{16}$, V or Z in the meaning of an alkyl group can be identical or different and straight-chain or branched, and are, in particular, low molecular weight alkyl groups having 1 to 7 and preferably 1 to 4 carbon atoms, such as methyl, ethyl, propyl, isopropyl, tert-butyl, amyl, hexyl, heptyl, or alkyl groups having a longer chain, such as octyl, decyl or dodecyl. Possible substituents are, for example, the following: hydroxyl, low molecular weight alkoxy or carbalkoxy, phenoxy, cyano, carboxamido, halo-en, in particular chlorine or bromine, and acetoxy. $R_1$ and $R_2$ advantageously denote methyl or ethyl. $V_1$, $V_1'$, $T_1$–$T_{16}$, V or Z in the meaning of a cycloalkyl group represent, in particular, the cyclohexyl or methylcyclohexyl group, and in the meaning, of an aralkyl group represent, above all, the benzyl, phenethyl or β-phenyl-β-hydroxyethyl group.

If $R_1$ and $R_2$ or Z, and $Z_2$, together with the nitrogen atom and optionally including further hetero atoms, such as O, S or N, form a 5- to 7-membered hetero ring, this is, for example, the piperidine, pyrrolidine, morpholine, triazole, piperazine or N-methyl-piperazine ring.

If $R_1$ or $R_2$, together with the nitrogen, forms a radical fused-on in the ortho-position relative to the nitrogen of ring A, this is preferably the following groupings:

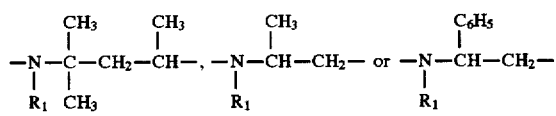

If R, $T_1$–$T_{16}$ or Z denotes an aryl radical, this is, for example, the naphthalene and preferably the phenyl radical.

Possible substituents on the aryl, in particular phenyl, and also benzo radicals are: one or more alkyl groups, such as methyl, ethyl or isopropyl, alkoxy groups, such as methoxy or ethoxy, acylamino groups, such as acetylamino or benizoylamino, halogen atoms, such as chlorine or bromine, hydroxyl, cyano, thiocyano, amino mono- and di-alkylamino, phenylamino, N-phenyl-N-alkylamino, phenyl, phenoxy, nitro, acyl or acyloxy, such as acetyl or acetoxy. Methyl or ethyl are preferred.

The substituted carboxamide or sulphonamide groups preferably contain 1 to 10 carbon atoms and are preferably N-methyl-, N,N-dimethyl-, N,ethyl-, N,N-diethyl-, N-benzyl and N-phenylcarboxamide or -sulphonamide.

A large number of organic and inorganic cyanides and cyanide-donating compounds are in principle suitable for carrying out the process according to the invention. Cyanides of the first and second main group and sub-group of the periodic table of the elements as well as ammonium cyanide and ammonium cyanides substituted by alkyl, aryl or aralkyl are particularly suitable. Examples which may be mentioned are:

Ca(CN)$_2$, Zn(CN)$_2$, NH$_4$CN, Na[Cu(CN)$_2$], (n-C$_4$H$_9$)$_4$NCN and, in particular, KCN and NaCN.

Possible cyanides are also compounds which split off cyanide, such as, for example, hydroxyacetonitrile, nitromethane or formaldehyde oxime. It is furthermore possible to employ the cyanides mentioned in any desired mixtures with one another.

Equivalent amounts of cyanides are usually employed for carrying out the process according to the invention. However, it is sometimes advantageous to employ an excess of 1 to 100%. The cyanides can be employed in solid form or also as a solution in a solvent, such as, for example, water, methanol, ethanol, DMF, NMP, dimethylacetamide or caprolactam. The use of the cyanides in aqueous solution is preferred.

Suitable solvents for carrying out the process according to the invention are in principle polar and non-polar solvents.

Polar solvents which may be mentioned are, for example: protic solvents, such as, for example, water and alcohols, and aprotic solvents, such as, for example, dimethylformamide, N-methylpyrrolidone, acetone and dioxane, the following polar solvents being preferred: water, alcohols, pyridine, picoline, dimethylformamide, N-methylpyrrolidone, dimethylsulphoxide and acetonitrile. The polar solvents can be employed in any desired mixtures with one another.

Non-polar solvents which may be mentioned are: alkanes, toluene, xylene, chlorobenzene, dichlorobenzene and methylene chloride.

The use of polar solvents, in particular as a mixture with water, is preferred. The following mixtures are to be singled out in particular: dimethylformamide/water, N-methylpyrrolidone/water and dimethylsulphoxide/water.

In some cases it may prove advantageous to add a phase transfer catalyst to the polar or the non-polar solvent or the mixture of water and another polar solvent.

Possible phase transfer catalysts are, for example: quaternary ammonium salts, phosphonium salts, polyethylene glycol, crown ethers, amines and phosphonium compounds.

The phase transfer catalyst is usually employed in amounts of 0.1 to 2 molar equivalents, based on the educt employed, preferably 0.5 to 1.5 molar equivalents.

The reaction temperatures for this first component step are 0° to 100° C., preferably 20° to 80° C. The intermediate product formed in this component step can be isolated under suitable protective measures (for example exclusion of water), but is preferably reacted directly.

Suitable acids are organic or inorganic in nature, preferably carboxylic acids, and particularly preferably mineral acids. Examples which may be mentioned are: acetic acid, hydrochloric acid, sulphuric acid, phosphoric acid, hydrobromic acid and hydriodic acid.

The amount of acid employed can be varied widely, but is preferably between 10 and 200 mol %, based on the starting material of the formula (II), but an equivalent amount is preferably employed.

Suitable halides are organic and inorganic halogen compounds, such as, for example, chlorides, bromides and iodides of alkali metals, and of these bromide is preferred. In addition to organic halides, such as, for example, tetraalkyl-ammonium halides, inorganic halides are preferably suitable for reasons of accessibility, costs, disposal and solubility. Of these, the halides of the first and second main group of the periodic table are preferred, and among these in turn those of the first main group. Examples are NaCl, NaBr, KCl and KBr, but also FeCl$_3$, ZnCl$_2$, ZnBr$_2$, MgCl$_2$ or NH$_4$Br. The amount of halide to be employed is 0.1 to 200 mol %, based on the educt (II), preferably 10 to 100%.

The halide can advantageously also be employed in a catalytic amount of only 0.1 to 0.6 mol %, based on the educt (II). The lower costs of using halide and lower pollution of the mother liquor after the reaction with halide are to be emphasized here.

The oxidizing agents possible for the process according to the invention are other than Br$_2$. Apart from this proviso, all oxidizing agents are in principle possible, especially those which have a chemical potential of at least 0.1 eV, preferably greater than 0.4 eV. Examples which may be mentioned are: peracids, persulphates, peroxides, chloranil, nitric acid, peroxide addition compounds, such as, for example, perborate, or atmospheric oxygen in the presence of suitable catalysts, such as, for example, V$_2$O$_5$. The oxidizing agent can be employed in bulk or as a solution, preferably as an aqueous solution.

Preferred oxidizing agents are hydrogen peroxide and the compounds derived therefrom. Hydrogen peroxide is preferably employed in aqueous, dilute or concentrated form. 20 to 50% strength aqueous solutions are preferred. The amount of oxidizing, agent is preferably equivalent to the educt of the formula (II), and excesses of up to 50% can also be beneficial. The oxidizing agents mentioned can also be employed as a mixture with one another.

The reaction temperature for the component step of oxidation is in general −20° to 150° C., preferably 0° to 100° C., particularly preferably 20° to 90° C.

The compounds (II) are known (cf. DE-A-2 844 299), or they can be prepared in a known manner.

Two particularly preferred process variants are described below:

According to variant A, the acid is added to a solution or suspension of the cyanide addition product of the formula (IV)

and the halide and then the oxidizing agent are added.

According to variant B, the acid, halide and oxidizing agent are preferably initially introduced into the reaction vessel in a solvent and the cyanide addition product (IV) is added. This process offers the advantage that the competing reaction of splitting of (IV) back into (II) is suppressed.

In a refinement of variant B, the acid, halide and only some (for example 5 to 50%) of the oxidizing, agent are initially introduced into the reaction vessel and the cyanide addition product (IV) and the remainder of the oxidizing agent are added at the same time.

In a further refinement of variant B, the addition of the oxidizing agent is controlled via a redox electrode such that, by monitoring of the redox potential, an excess of the oxidizing, agent is always present.

The process according, to the invention renders possible, for example, large-scale industrial synthesis of dyestuffs which are outstandingly suitable for dyeing or printing, on synthetic and semi-synthetic textile material, for example of polyamides, triacetate and, in particular, polyesters, and for bulk dyeing of plastics. Dyestuffs which can easily be sublimed and are used for transfer printing on textile and non-textile substrates, such as, for example, cellulose triacetate, polyacrylonitrile and, in particular, polyester materials, can likewise be prepared by the process according to the invention. In addition, the dyestuffs prepared by the process according to the invention can also be employed in the D2T2 process (Dye-Diffusion-Thermal Transfer).

The invention therefore likewise relates to a process for dyeing or printing, on synthetic or semi-synthetic textile material, bulk dyeing of plastics, transfer printing on textile and non-textile substrates and thermo-transfer, characterized in that dyestuffs which are obtained by the preparation process according to the invention are used. The invention furthermore relates to substrates which have been obtained by one of the above printing or dyeing processes using the dyestuffs prepared according to the invention.

The dyestuffs are obtained in an excellent purity and with very good yields by the process according to the invention.

The following examples are intended to illustrate the process according to the invention but without limiting it thereto.

EXAMPLE 1

70.2 g of the dyestuff of the formula

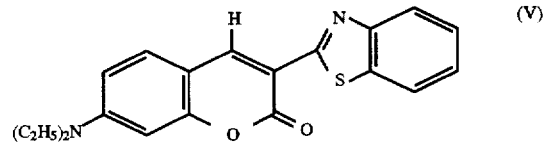

were suspended in 352 ml of N-methylpyrrolidone (NMP). 10.8 g of sodium cyanide, dissolved in 18 ml of water, were added to this suspension. The temperature rose to about 35° C. The mixture was subsequently stirred at 45° C. for about 1 hour. During this operation, the dyestuff dissolved. 10.4 g, of sodium bromide were initially introduced into 200 ml of N-methylpyrrolidone with 20.4 g, of $H_2SO_4$ (96% strength) and 21.4 g of hydrogen peroxide (34% strength). The solution of the cyanide addition product was added dropwise to this mixture. During, this operation, the temperature rose to about 70° C. After cooling, the dyestuff was filtered off and washed with methanol and water. After drying, 70.9 g, of the dyestuff of the formula

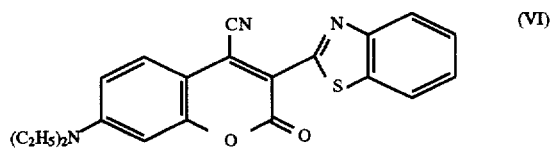

were obtained.

EXAMPLE 2

350.5 g of the dyestuff of the formula (V) according to Example 1 were suspended in 1760 ml of N-methylpyrrolidone. A solution of 53.9 g of NACN in 90 ml of water was added at 20° to 25° C. The mixture was subsequently stirred at 40° to 45° C. for 1 hour. During, this operation, the dyestuff dissolved. 51.5 g, of sodium bromide, 56 ml of $H_2SO_4$ (96% strength) and 94.2 ml of hydrogen peroxide (35% strength) were added to the solution at 0° C. During this operation, the temperature rose to 80° to 85° C. The dyestuff (VI) was then isolated analogously to Example 1. 361.4 a were obtained.

EXAMPLE 3

If dimethylformamide was used instead of N-methylpyrrolidone and the procedure was otherwise the same as that described in Example 1, 70.2 g of dyestuff (VI) were obtained.

EXAMPLE 4

If dimethylformamide was used instead of N-methylpyrrolidone and the procedure was otherwise the same as that described in Example 2, 360 g of dyestuff (VI) were obtained.

EXAMPLE 5

A solution of 27 g of sodium cyanide in 46 ml of water was added dropwise to a suspension of 185 g of the dyestuff of thee formula

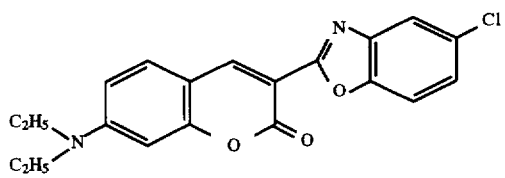

in 1 l of N-methylpyrrolidone. The mixture was subsequently stirred at 35° C. for 2 hours.

30.5 ml of 96% strength sulphuric acid and then 5 ml of 35% strength hydrogen peroxide were added dropwise at 20° C. to a suspension of 57 g of sodium bromide in 500 ml of N-rmethylpyrrolidone (NMP). The solution of the cyanide addition product and 42 ml of 35% strength hydrogen peroxide were allowed to run in simultaneously in the course of 1 hour, while stirring, and cooling at 25° C. The mixture was subsequently stirred for 30 minutes, the excess hydrogen peroxide was removed with a few ml of sodium bilsulphite solution, the mixture was rendered neutral with 60 ml of 30% strength sodium hydroxide solution and the dyestuff was filtered off with suction. It was washed with methanol and water and dried at 50° C. Yield 180 g; melting point 234° to 234.5° C.

EXAMPLE 6

If sodium bromide was used in a catalytic amount of 2.8 g and the procedure was otherwise the same as that described in Example 1 or 2, the reaction time was prolonged by about 30 minutes to 2 hours. The yield was comparable.

EXAMPLE 7

If equimolar amounts or an excess of sodium bromide (about 1–200%) were used instead of catalytic amounts of sodium bromide and the procedure was otherwise the same as that described in Example 1 or 2, comparable yields were obtained.

The same results were obtained if potassium bromide, lithium bromide, ammonium bromide, sodium iodide, potassium iodide, lithium iodide or sodium chloride were used as described in Examples 1 to 7 instead of sodium bromide, in similar ratios of amounts to those described in Examples 1–7.

The following, compounds can be prepared analogously to Example 1:

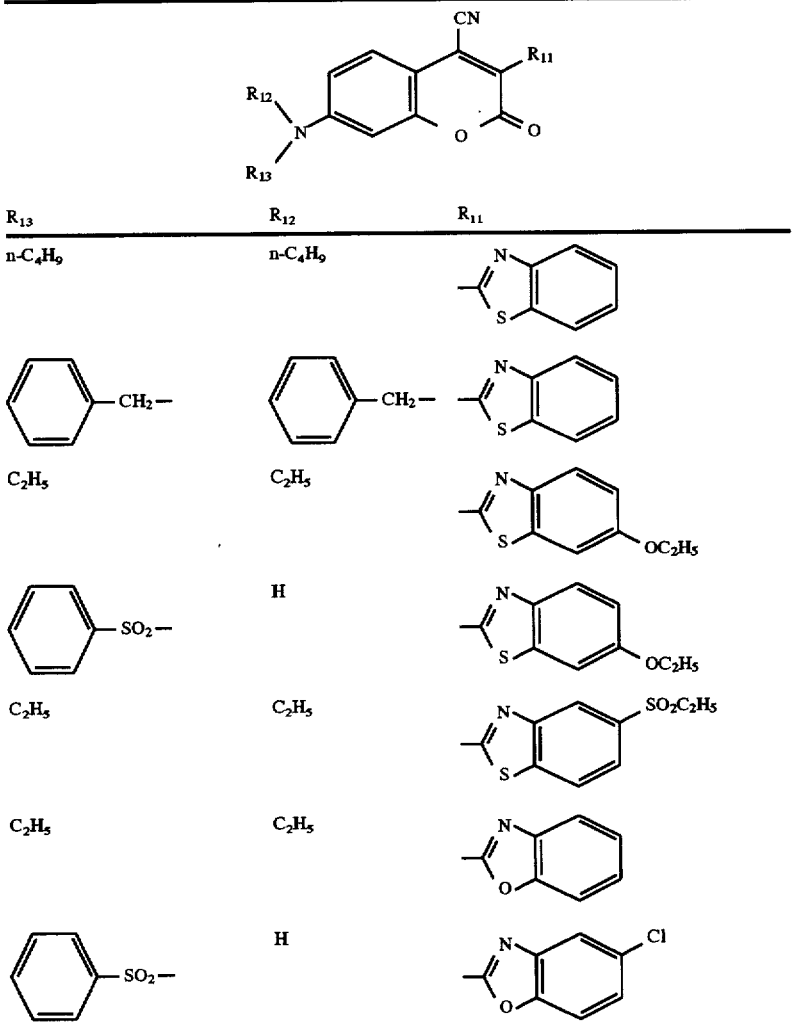

-continued

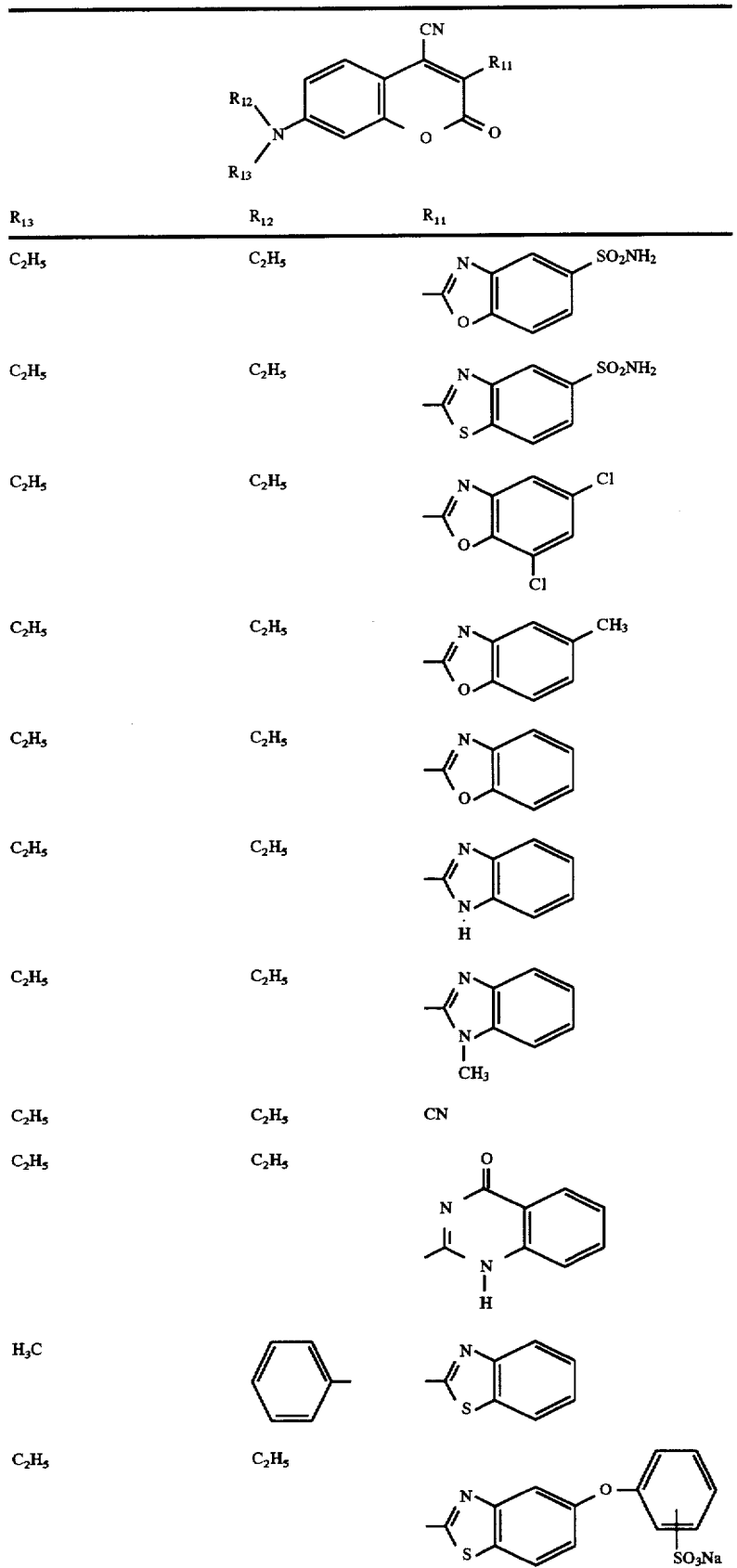

| $R_{13}$ | $R_{12}$ | $R_{11}$ |
|---|---|---|
| $C_2H_5$ | $C_2H_5$ | 2-methyl-benzoxazole-5-sulfonamide |
| $C_2H_5$ | $C_2H_5$ | 2-methyl-benzothiazole-5-sulfonamide |
| $C_2H_5$ | $C_2H_5$ | 2-methyl-5,7-dichloro-benzoxazole |
| $C_2H_5$ | $C_2H_5$ | 2-methyl-5-methyl-benzoxazole |
| $C_2H_5$ | $C_2H_5$ | 2-methyl-benzoxazole |
| $C_2H_5$ | $C_2H_5$ | 2-methyl-benzimidazole (NH) |
| $C_2H_5$ | $C_2H_5$ | 2-methyl-1-methyl-benzimidazole |
| $C_2H_5$ | $C_2H_5$ | CN |
| $C_2H_5$ | $C_2H_5$ | 2-methyl-quinazolinone |
| $H_3C$ | phenyl | 2-methyl-benzothiazole |
| $C_2H_5$ | $C_2H_5$ | 2-methyl-5-(phenoxy-sulfonate-Na)-benzothiazole |

-continued

| R13 | R12 | R11 |
|---|---|---|
| C2H5 | C2H5 | (N=C(Cl)=C(Cl)- thiazoline group) |
| C2H5 | C2H5 | (N=C(C6H5)-N thiazole group) |
| PhSO2— | H | 5-methyl-benzoxazol-2-yl |
| PhSO2— | H | benzothiazol-2-yl |
| PhSO2— | H | 1-methyl-benzimidazol-2-yl |
| 4-CH3-C6H4-SO2— | H | benzothiazol-2-yl |
| 3,4-Cl2-C6H3-SO2— | H | 6-methoxy-benzothiazol-2-yl |
| NC—CH2—CH2— | NC—CH2—CH2— | benzothiazol-2-yl |
| C6H11-OCH2—CH2— | H | benzothiazol-2-yl |
| C2H5 | C2H5 | (N—N, S, phenyl thiadiazoline) |
| C4H9 | C4H9 | (N—N, S, 3-chlorophenyl thiadiazoline) |

The following compounds can be prepared analogously to Examples 1 and 2:
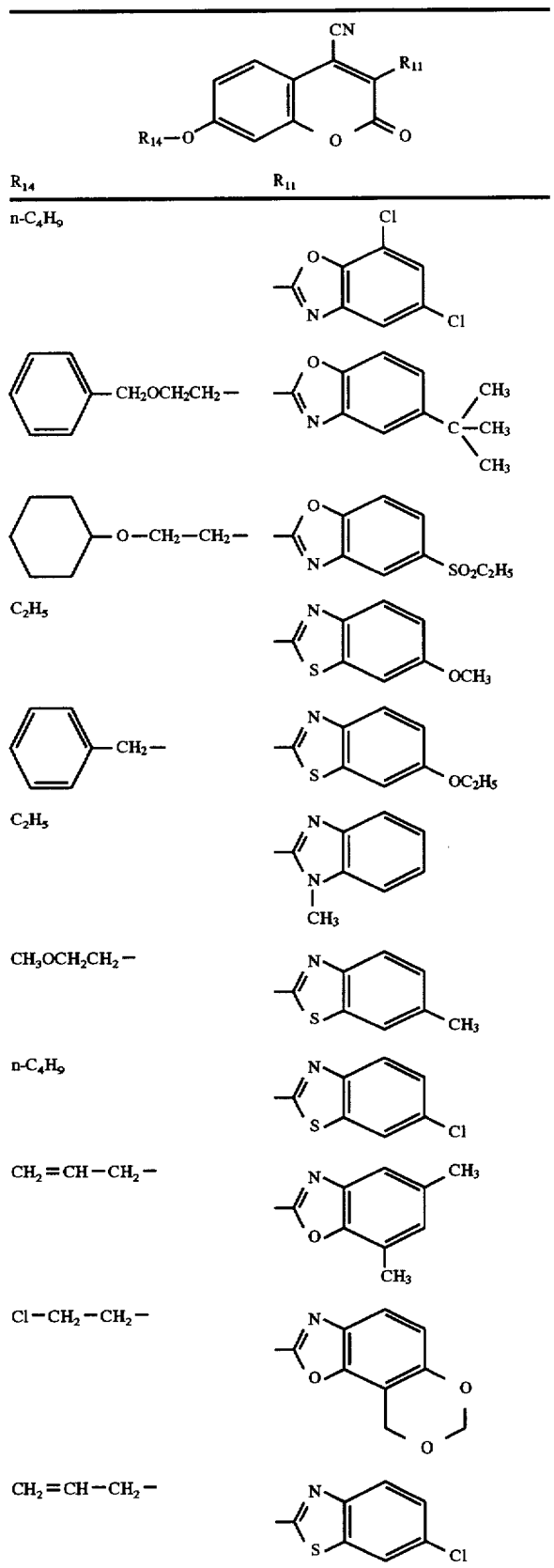
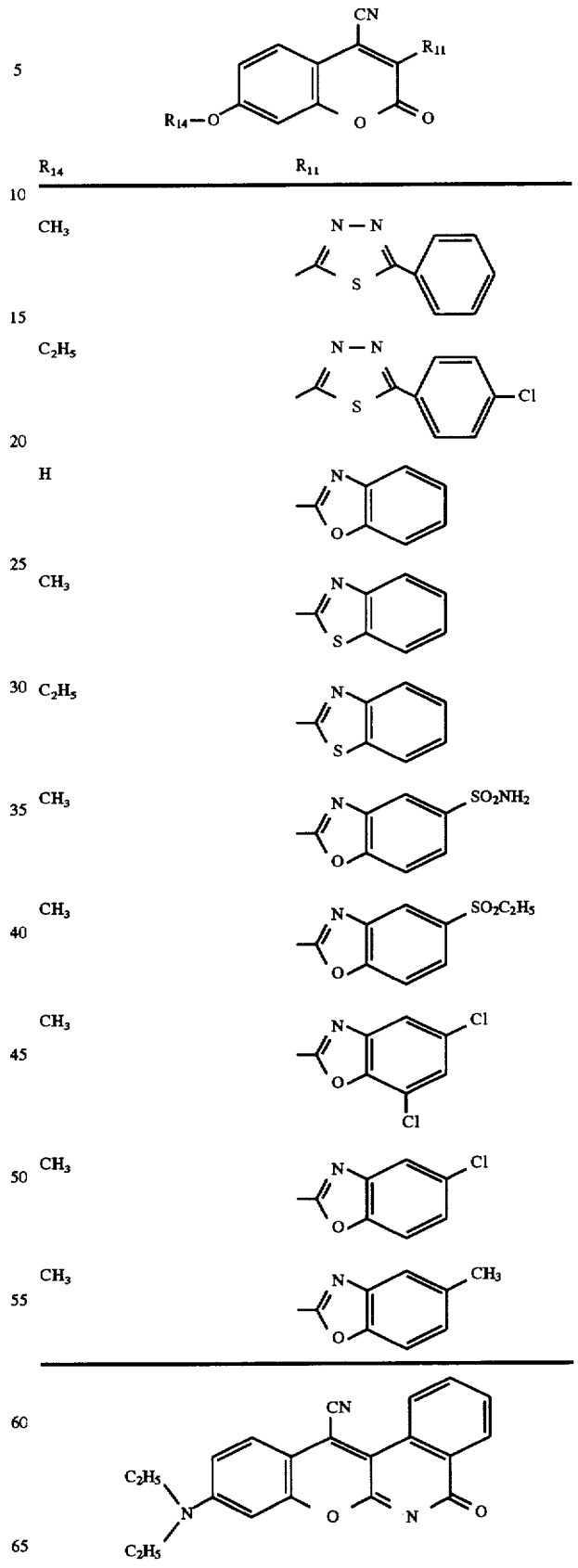

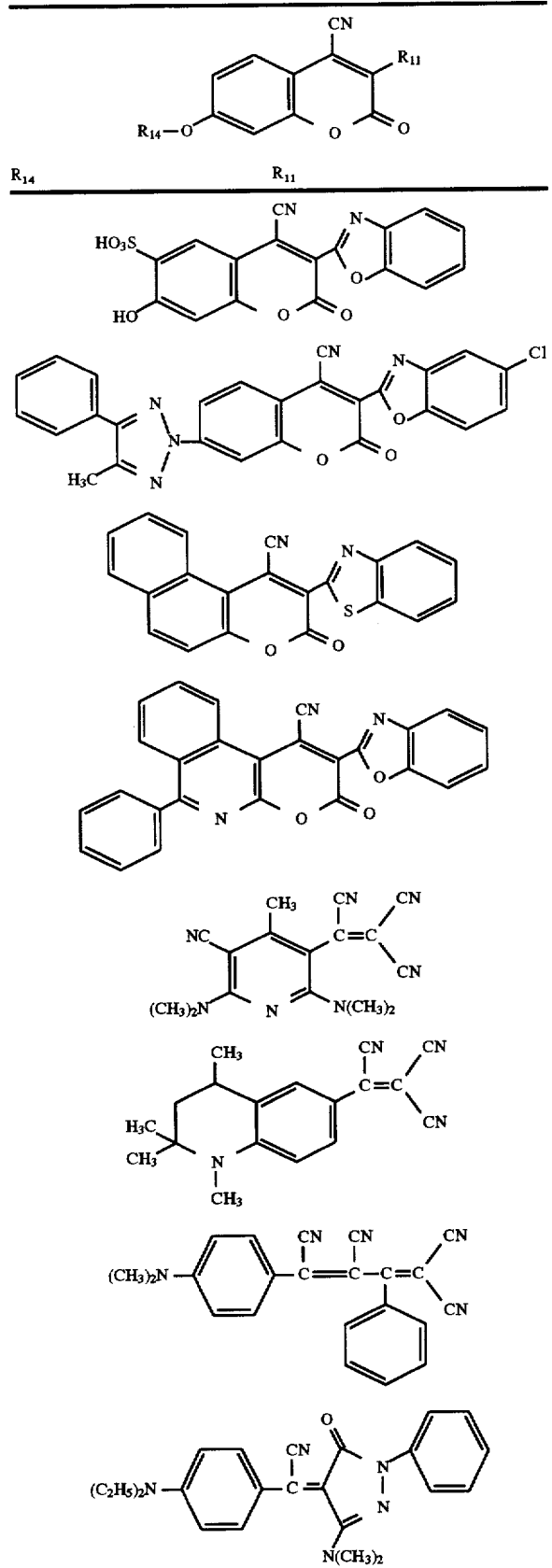
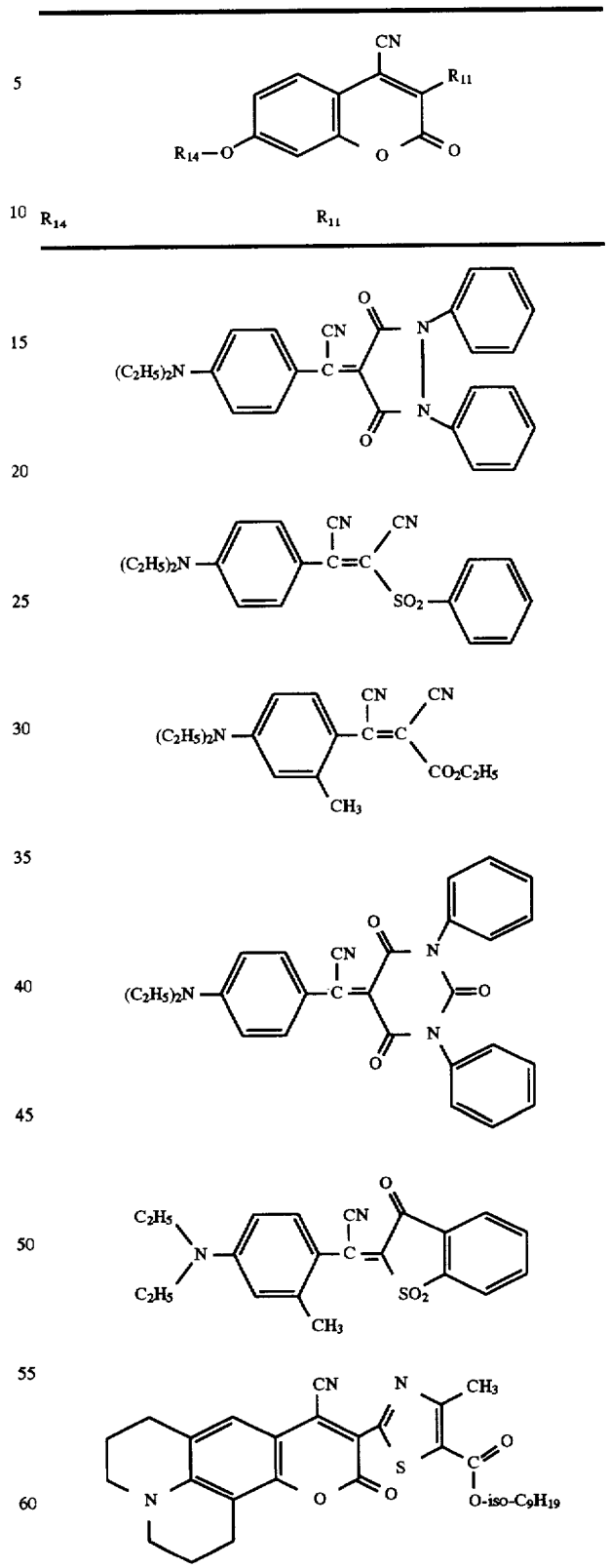

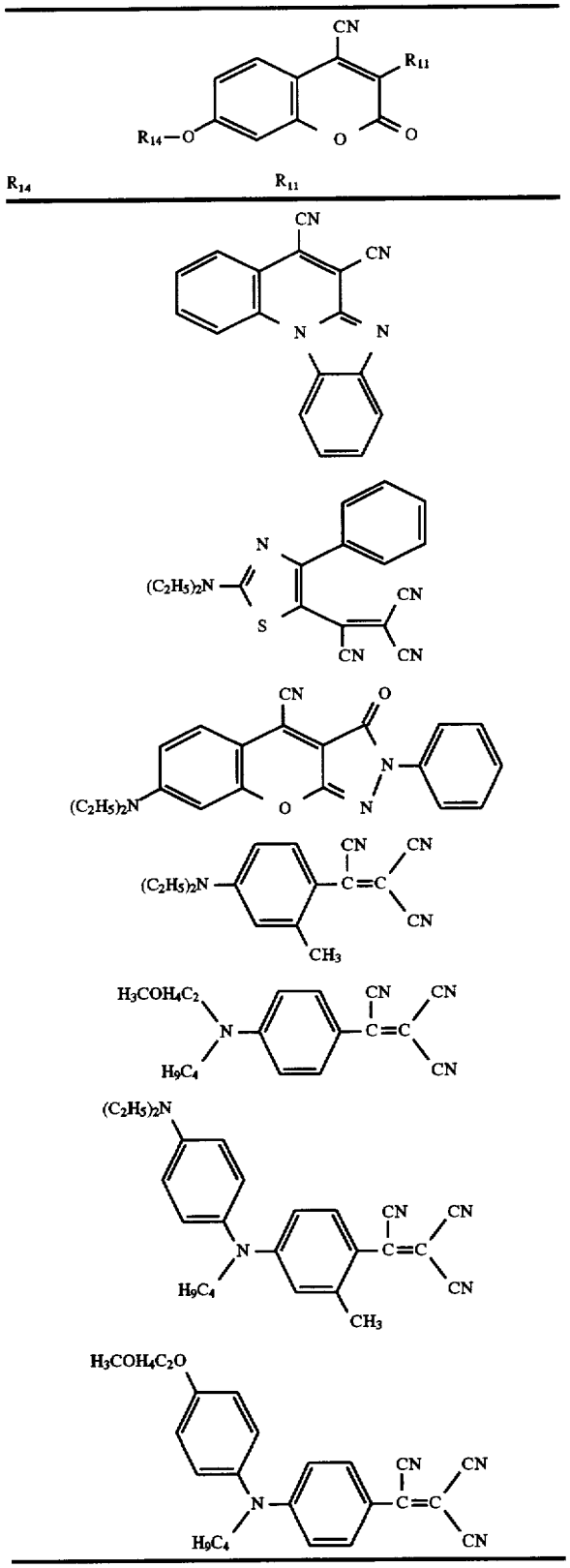

We claim:

1. Process for the preparation of compounds of the formula

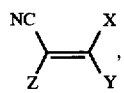

in which

X and Y independently of one another represent an electron-attracting radical, or X and Y, together with the carbon atom to which they are bonded, form an optionally substituted, heterocyclic or carbocyclic ring, Z represents unsubstituted or substituted, optionally fused aryl or represents an unsubstituted or substituted, optionally fused heterocyclic radical, or Y and Z, together with the carbon atoms to which they are bonded and including the double bond, form an unsubstituted or substituted heterocyclic radical, wherein compounds of the formula

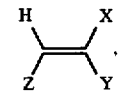

wherein

X, Y and Z have the abovementioned meaning, are reacted with a cyanide or a cyanide-donating compound and then with an oxidizing agent other than $Br_2$ in the presence of halides.

2. Process according to claim 1, wherein compounds of the formula II are reacted with a cyanide or a cyanide-donating compound and then with an oxidizing, agent other than $Br_2$ in the presence of halides and acid.

3. Process according to claim 1, wherein X and Y independently of one another denote a radical of which the Hammett substituent constant σ (para) >0.

4. Process according to claim 1, wherein compounds of the formula (I) wherein

X represents cyano, —CO—$OV_1$,

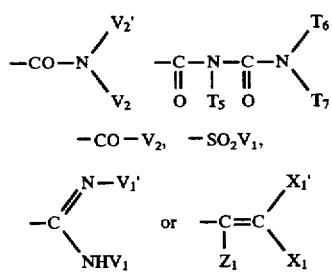

wherein $V_1$ and $V_1'$ independently of one another represent alkyl, cycloalkyl, alkenyl, aralkyl or aryl, $T_5$, $T_6$ and $T_7$ independently of one another denote hydrogen or unsubstituted or substituted aryl, $V_2$ and $V_2'$ independently of one another represent H or $V_1$, or $V_1$ and $V_1'$ or $V_2$ and $V_2'$, in each case together with the radicals to which they are bonded, represent a 5- or 6-membered, unsubstituted or substituted unsaturated, heterocyclic radical which contains 1 to 3 identical or different hetero atoms from the series consisting of O, N and S and is optionally fused by a substituted or unsubstituted benzene ring., or represent a 5- or 6-membered, unsubstituted or substituted unsaturated carbocyclic radical, or phenyl, $X_1$ and $X_1'$ independently of one another represent

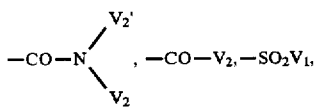, $-CO-V_2, -SO_2V_1$,

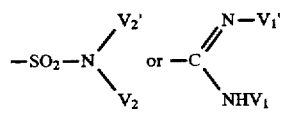

wherein $V_1$, $V_1'$, $V_2$ and $V_2'$ have the abovementioned meaning, or $X_1$ and $X_1'$, together with the C atom to which they are bonded, represent a 5- or 6-membered, unsubstituted or substituted heterocyclic radical which contains 1 or 2 N atoms and is optionally fused by a further 5-membered unsaturated heterocyclic radical or a benzene ring, Z represents unsubstituted or substituted $C_6$–$C_{10}$-aryl, which is optionally fused by a saturated or unsaturated heterocyclic radical, or represents an unsaturated 5- or 6-membered, unsubstituted or substituted heterocyclic radical which contains 1 to 4 identical or different hetero atoms from the series consisting of O, N and S optionally fused by a benzene ring, or $Z_1$ and $X_1$, together with the carbon atoms to which they are bonded and including the double bond, form an unsubstituted or substituted and optionally fused heterocyclic radical or an aromatic carbocyclic ring, or a benzene ring, Y is identical to or different from X, or X and Y, together with the C atom to which they are bonded, represent a 5- or 6-membered unsubstituted or substituted heterocyclic radical which contains 1 or 2 N atoms and which can optionally be fused by a further 5-membered unsaturated heterocyclic ring or a benzene ring, Z represents unsubstituted or substituted $C_6$–$C_{10}$-aryl, which is optionally fused by a saturated or unsaturated heterocyclic radical, or represents an unsaturated 5- or 6-membered unsubstituted or substituted heterocyclic radical which contains 1 to 4 identical or different hetero atoms from the series consisting of O, N and S optionally fused by a benzene ring, or Y and Z together, including the double bond to which they are bonded, form a 6-membered, unsubstituted or substituted heterocyclic radical which contains a hetero atom from the series consisting of O, N and S and is optionally fused by a substituted or unsubstituted benzene ring, where possible substituents for the carbocyclic and the heterocyclic radical are, in particular, alkyl, alkylsulphonyl, aryl, aralkyl, alkenyl, $-SO_2OR_1$, cycloalkyl, alkoxy, alkoxycarbonyl, acyl, halogen, cyano, C=O, C=NH, in each case optionally substituted carboxamide or sulphonamide, nitro or exocyclic =O or =NH, and possible substituents within the definition of X for the fused benzene ring are alkyl, $SO_2$-alkyl, optionally substituted sulphonamide-$SO_1NR_2R_2$, alkyl, aralkyl, cycloalkyl, alkoxy, alkoxycarbonyl, acyl, halogen, cyano, nitro or alkenyl, and where possible substituents for the aromatic carbocyclic radical or the heterocyclic radical in the definition of Z are

in which $R_1$ and $R_2$ independently of one another represent hydrogen, unsubstituted or substituted alkyl, alkenyl, cycloalkyl, aralkyl or aryl, or $R_1$ and $R_2$, together with the nitrogen atom to which they are bonded, form a 5- to 6-membered heterocyclic radical having 1 to 3 hetero atoms from the series consisting of O, N and S, are prepared.

5. Process according to claim 1, wherein the compounds (I) are those of the formula

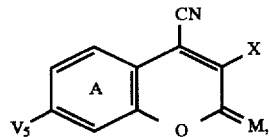 (IV)

in which $V_5$ represents

$OR_1$, $NHCOR_1$ or $NHSO_2R_1$, $R_1$ and $R_2$ independently of one another represent hydrogen, unsubstituted or substituted alkyl, cycloalkyl, aralkyl or aryl, or $R_1$ and $R_2$, together with the nitrogen atom to which they are bonded and optionally including further hetero atoms, form a 5- to 7-membered heterocyclic radical, or one of the radicals $R_1$ or $R_2$, with a carbon atom of ring, A in the o-position relative to the amino group, forms a fused-on, saturated, unsubstituted or substituted 5- or 6-membered ring, M represents $=NR_3$, $=NCOR_4$,

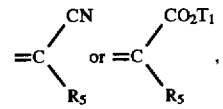

=NH or =O, wherein $R_3$ represents alkyl or unsubstituted or substituted phenyl, $R_4$ represents unsubstituted or substituted alkyl, aralkyl, aryl, vinyl, alkoxy, phenoxy or amino and $R_5$ represents carbalkoxy, cyano or optionally substituted carboxamide, or $R_5$, together with X, forms the remaining members of an unsaturated 6-membered, optionally fused N-heterocyclic radical, and X has the meaning given in claim 1.

6. Process according to claim 1, wherein an organic or inorganic cyano compound or a compound which splits off cyanide or a mixture of these compounds is employed as the cyanide.

7. Process according to claim 1, wherein at least one polar solvent, if appropriate in combination with a phase transfer catalyst, is employed as the solvent.

8. Process according to claim 1, wherein the oxidizing agent employed is one having a chemical potential of greater than 0.1 eV.

9. Process according to claim 1, wherein organic and/or inorganic compounds of chlorine, bromine or iodine are employed as halides in amounts of 0.1 to 200 mol %, based on the educt (II).

10. Process according to claim 2, wherein a carboxylic or mineral acid is employed as the acid.

11. Process according to claim 2, wherein the acid is first added to the solution of the reaction product of (II) with the cyanide and the halide and the oxidizing agent are then added in succession.

12. Process according to claim 2, wherein the acid, halide and oxidizing agent are initially introduced into the reaction vessel in the solvent and the reaction product of (I) with the cyanide is then added.

13. A process according to claim 4, wherein $T_5$, $T_6$ and $T_7$ independently of one another represent hydrogen or phenyl.

14. A process according to claim 4, wherein said $V_1$ and $V_1'$ or $V_2$ and $V_2'$ represent a 5 or 6-membered unsubstituted or substituted unsaturated aromatic heterocyclic radical.

15. A process according to claim 1, wherein the oxidizing agent employed is hydrogen peroxide.

* * * * *

UNITED STATES PATENT AND TRADEMARK OFFICE
CERTIFICATE OF CORRECTION

PATENT NO : 5,750,761
DATED : May 12, 1998
INVENTOR(S): Hamprecht, et al.

It is certified that error appears in the above-identified patent and that said Letters Patent is hereby corrected as shown below:

Col. 23, Line 23        Delete "Z" and substitute -- $Z_1$ --

Col. 26, Line 5         Delete "(I) and substitute --(II)--

Signed and Sealed this

Second Day of November, 1999

Attest:

Q. TODD DICKINSON

Attesting Officer        Acting Commissioner of Patents and Trademarks